United States Patent [19]

Burtis et al.

[11] Patent Number: 4,847,205
[45] Date of Patent: Jul. 11, 1989

[54] DEVICE AND METHOD FOR AUTOMATED SEPARATION OF A SAMPLE OF WHOLE BLOOD INTO ALIQUOTS

[75] Inventors: Carl A. Burtis, Oak Ridge; Wayne F. Johnson, Loudon, both of Tenn.

[73] Assignee: Martin Marietta Energy Systems, Inc., Oak Ridge, Tenn.

[21] Appl. No.: 36,038

[22] Filed: Apr. 8, 1987

[51] Int. Cl.$^4$ .................. B04B 5/02; B04B 11/00; B01D 21/26

[52] U.S. Cl. .................. 436/45; 422/72; 422/101; 422/102; 436/63; 436/177; 494/16

[58] Field of Search .................. 356/246, 427, 440; 422/72, 102; 436/45; 494/16, 17

[56] References Cited

U.S. PATENT DOCUMENTS

| | | | |
|---|---|---|---|
| 458,194 | 8/1891 | Sharples | 494/17 |
| 3,555,284 | 1/1971 | Anderson . | |
| 3,798,459 | 3/1974 | Anderson et al. . | |
| 3,854,508 | 12/1974 | Burtis et al. . | |
| 3,873,217 | 5/1975 | Anderson et al. | 422/72 |
| 3,890,101 | 6/1975 | Tiffany et al. . | |
| 4,035,156 | 7/1977 | Shumate, III | 422/72 |
| 4,515,889 | 5/1985 | Klose et al. | 435/4 |
| 4,557,600 | 12/1985 | Klose et al. | 356/246 |
| 4,740,472 | 4/1988 | Bartis et al. | 422/72 |

OTHER PUBLICATIONS

Burtis et al., "Development of a Simple Device for Processing Whole-Blood Samples . . . ", 32 Clinical Chem. 1672 (1986).

Primary Examiner—Michael S. Marcus
Attorney, Agent, or Firm—Bruce M. Winchell; James M. Spicer

[57] ABSTRACT

A device and a method for automated processing and separation of an unmeasured sample of whole blood into multiple aliquots of plasma. Capillaries are radially oriented on a rotor, with the rotor defining a sample chamber, transfer channels, overflow chamber, overflow channel, vent channel, cell chambers, and processing chambers. A sample of whole blood is placed in the sample chamber, and when the rotor is rotated, the blood moves outward through the transfer channels to the processing chambers where the blood is centrifugally separated into a solid cellular component and a liquid plasma component. When the rotor speed is decreased, the plasma component backfills the capillaries resulting in uniform aliquots of plasma which may be used for subsequent analytical procedures.

15 Claims, 1 Drawing Sheet

DEVICE AND METHOD FOR AUTOMATED SEPARATION OF A SAMPLE OF WHOLE BLOOD INTO ALIQUOTS

BACKGROUND OF THE INVENTION

The present invention relates to a device for automated processing of an unmeasured sample of whole blood into measured multiple aliquots of plasma, and to a method for accomplishing such processing.

To analyze a sample of whole blood for its chemical content, it is first necessary to separate the liquid plasma component from the solid cellular component, and then to divide the plasma into discrete aliquots for further processing. Traditionally, this is a multistep, labor-intensive process which requires not only manual operations, but also some type of pipetting equipment for the final aliquoting step. As a result, the existing methods and equipment for preparing aliquots of plasma from whole blood are expensive and inefficient.

Centrifugal fast analyzers are known devices. For example, see U.S. Pat. Nos. 3,555,284; 3,798,459; 3,864,089; and 3,890,101. However, none of these known devices has proved to be completely satisfactory. Thus, there exists a need for a device which will, in a single step, automatically separate whole blood into multiple, and uniform, aliquots of plasma suitable for efficient subsequent analytical procedures.

Commonly owned, copending application Ser. No. 762,368, filed on Aug. 5, 1985, describes a device for use with a centrifugal fast analyzer which employs two sets of capillaries to avoid the problems inherent in the prior art. In this device, blood is introduced into the analyzer via a first set of capillaries which have been prefilled with unmeasured amounts of blood. When centrifugal force is applied, the blood flows out of the first capillaries into a processing chamber where it is separated into plasma and cellular phases. When the centrifugal force is released, the plasma backflows into the measuring capillaries. This device has the disadvantage that it is necessary to prefill a set of capillaries prior to processing.

SUMMARY OF THE INVENTION

Accordingly, one object of the present invention is to provide a device for automated separation of an unmeasured sample of whole blood into multiple aliquots of plasma.

Another object of the present invention is to provide a device capable of separating an unmeasured sample of whole blood into measured aliquots of plasma in a single automatic operation.

Still another object of the present invention is to eliminate the need for expensive pipettors to prepare measured aliquots of plasma.

Still another object of the present invention is to provide a means for obtaining uniform aliquots of plasma without incurring leakage.

These and other objects of the invention are achieved by providing a device for automated separation of an unmeasured sample of whole blood into multiple aliquots of plasma, comprising:
(a) a rotor having a central axis and means for receiving a plurality of capillaries disposed radially around the central axis, with said capillaries each having a radially outwardly oriented end and a radially inwardly oriented end; said rotor defining:
  (i) a sample chamber for receiving an unmeasured sample of whole blood;
  (ii) a plurality of processing chambers disposed around the circumference of the rotor so as to register with the outward ends of capillaries received in said receiving means;
  (iii) a plurality of transfer channels each communicating between the sample chamber and one of the processing chambers; and
(b) means for rotating the rotor at a speed sufficient to centrifugally separate a sample of whole blood in one of said processing chambers into a plasma component and a solid cellular component.

The objects of the invention are further achieved by providing a method for automated processing and separation of an unmeasured sample of whole blood into multiple aliquots of plasma, comprising the steps of:
(a) introducing a sample of whole blood into a sample chamber in a rotor, said rotor having a central axis and means for receiving a plurality of capillaries disposed radially around the central axis with the capillaries each having a radially outwardly oriented end and a radially inwardly oriented end, said rotor defining a plurality of processing chambers disposed around the circumference of the rotor so as to register with the outward ends of capillaries received in said receiving means, and a plurality of transfer channels each communicating between the sample chamber and one of the processing chambers;
(b) rotating the rotor at a speed sufficient to distribute the blood radially outward from the sample chamber, through the transfer channels, into the processing chambers, and therein to centrifugally separate the blood into a plasma component and a solid cellular component;
(c) reducing the rotation speed of the rotor to allow the plasma component to backfill into the capillaries;
whereby the capillaries are filled with aliquots of plasma which may be used for further analyses.

DETAILED DESCRIPTION OF THE PREFERRED EMBODIMENTS

The invention comprises a device and a method for automated separation of an unmeasured sample of whole blood into multiple aliquots of plasma in a single operation.

Figure 1:
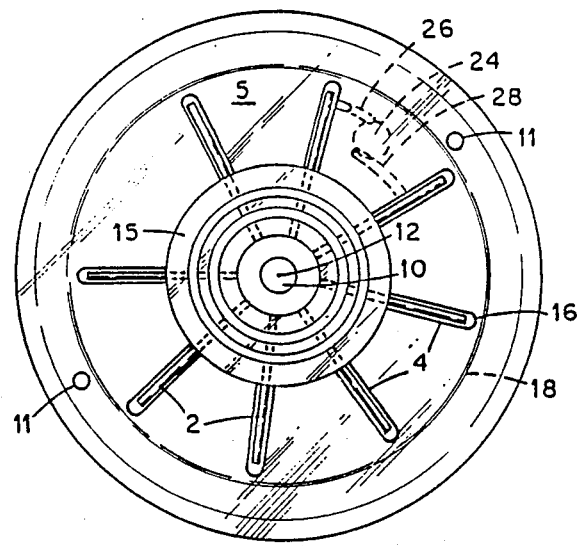
FIG. 1 shows a plan view of a device according to the present invention.
Figure 2:
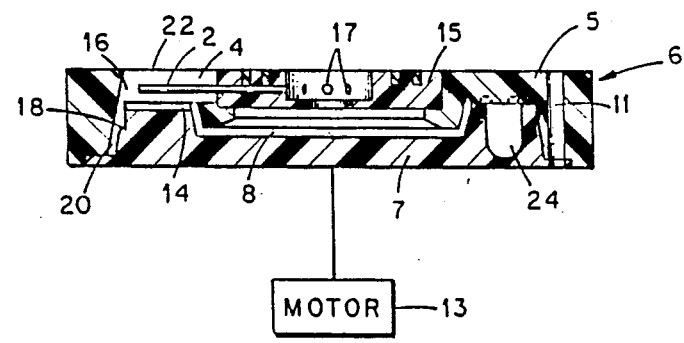
FIG. 2 shows a cross section through the rotor of the device of FIG. 1.

As shown in FIGS. 1 and 2, a rotor 6, comprises an upper portion 5 and a lower portion 7 sealed together before use. Proper positioning of the rotor is maintained by indexing pins inserted in indexing slots 11. Rotor 6 is rotatable about its central axis 12 by a motor 13. The rotor 6 has a capillary receptacle 15 for receiving a plurality of capillaries 2 with their ends protruding outwardly into recesses 4 formed in the upper surface of rotor portion 5. The recesses 4 may be sealed with clear adhesive tape 22 or other desired closure means. The rotor defines a central sample chamber 8 in which is placed an unmeasured sample of whole blood. The blood sample is introduced into the sample chamber 8 via inlet 10, which extends through the receiving means 15 and the upper portion 5 of rotor 6. A plurality of processing chambers 16 are disposed around the circumference of rotor 6. Sample chamber 8 communicates with the processing chambers 16 through a plurality of transfer channels 14 within the rotor. Each of the processing chambers 16 may also communicate with a cell chamber 20 in which the solid cellular component of whole blood is compacted and separated from the liquid plasma component. Cell chamber 20 preferably slants downwardly and outwardly to further increase the separation of cells and plasma.

In a particularly preferred embodiment, a circumferential distribution channel 18 is provided around the circumference of the rotor to ensure even distribution of blood to the processing chambers. The rotor may also include a vent system to further ensure even distribution of blood within the device. The vent system comprises an overflow chamber 24 which communicates with at least one processing chamber 16 via an overflow channel 26. The overflow chamber 24 in turn communicates with the atmosphere via a vent channel 28 which opens into one of the capillary recesses 4 in rotor 6.

In a preferred embodiment, the capillary receptacle 15 comprises a disk which is removably mounted within the rotor 6. Capillaries 2 may be removably inserted in a plurality of radial bores 17 provided in the disk. In this way, empty capillaries may be fitted onto the rotor easily, and filled capillaries also may be removed easily.

The operation of the preferred embodiment of the invention is as follows. The upper portion 5 and lower portion 7 of the rotor 6 are assembled and sealed. Capillaries 2 are arranged in radial bores 17 of capillary receptacle 15, and the receptacle with the capillaries is mounted on the rotor 6. The capillaries 2, which extend into recesses 4 in the upper portion 5 of rotor 6, are radially oriented. With the rotor 6 at rest, an unmeasured sample of whole blood is introduced through inlet 10 into sample chamber 8. The recesses 4, in which capillaries 2 are located, are sealed with adhesive tape 22 or other suitable means. The rotor 6 is then rotated about its central axis 12 by electric motor 13 or some other suitable drive mechanism such as an air motor. Motor 13 may be either a single speed or a variable speed type. If desired, a digital electronic motor controller may be provided to enable programming of the desired speed and time of rotation.

As the rotor starts to spin, the blood in the sample chamber 8 moves radially outwardly through transfer channels 14 to multiple processing chambers 16. In a preferred embodiment, even distribution of blood in the processing chambers is ensured by providing a distribution channel 18 around the circumference of the rotor and communicating with the processing chambers, which allows excess blood from one chamber to flow into an adjacent chamber.

Even distribution of the blood in the processing chambers is also facilitated by providing a vent system in the rotor. In a preferred embodiment, the vent system comprises an overflow chamber 24 which is connected to one of the processing chambers 16 by an overflow channel 26. The overflow chamber 24 communicates with the atmosphere by means of a vent channel 28 which terminates in a recess 4 in the rotor 6. The vent system hinders formation of air pockets which could interfere with even distribution of the blood in the processing chambers.

After the blood has filled all the processing chambers evenly up to the radius of the overflow channel 26, the rotation of the rotor is maintained in order to centrifugally separate the whole blood into a solid cellular component and a liquid plasma component. Efficient separations can be achieved, for example, with rotors from about 1 to 15 inches diameter rotated at speeds from about 2400 to 3500 revolutions per minute for about 3 to 7 minutes. In a preferred embodiment, a three inch diameter rotor is rotated at a speed of about 3000 revolutions per minute for about 5 minutes. The centrifugal force generated by the rotor's rotation causes the solid cellular component to be compressed on the outside of the processing chambers while the liquid plasma component remains on the inside in direct contact with the outward ends of the capillaries 2. In a preferred embodiment, the solid cellular component fills multiple cell compartments 20, one of which communicates with each processing chamber 16.

When the separation of the blood components is complete, the rotor speed is decreased, causing the plasma component to backfill each of the capillaries 2 by capillary action. When the rotor stops, the tape 22 or other closure means is peeled off, and the capillaries 2 are removed. The capillaries contain measured aliquots of plasma which may be used for analytical purposes requiring discrete, ultraprecise aliquots of plasma.

The foregoing description of preferred embodiments of the invention has been presented for purposes of illustration and description only. It is not intended to be exhaustive or to limit the invention to the precise forms disclosed, and obviously many modifications and variations are possible within the scope and limit of the above teaching. It is intended that the scope of the invention be defined by the appended claims and equivalents.

What is claimed is:

1. A device for automated processing and separation of an unmeasured sample of whole blood into multiple aliquots of plasma, comprising:
   (a) a rotor having a central axis, a plurality of removable capillary tubes and means for receiving said plurality of removable capillary tubes disposed radially around said central axis, with said capillaries each having a radially outwardly oriented end and a radially inwardly oriented end, said rotor defining;
      (i) a sample chamber for receiving an unmeasured sample of whole blood,
      (ii) a plurality of processing chambers disposed around the circumference of said rotor so as to register with the outward ends of removable capillary tubes received in said receiving means,
      (iii) a plurality of transfer channels each communicating between said sample chamber and one of said processing chambers;
   (b) means for rotating said rotor at a speed sufficient to centrifugally separate a sample of whole blood in one of said processing chambers into a plasma component and a solid cellular component; and
   (c) control means for regulating rotor speed to facilitate back filling of said removable capillary tubes.

2. A device as claimed in claim 1, wherein said rotor further defines a circumferential distribution channel disposed around the circumference of said rotor and communicating between said transfer channels adjacent said processing chambers.

3. A device as claimed in claim 1, wherein said rotor further defines a plurality of downwardly outardly slanting cell chambers, each of said cell chambers communicating with one of said processing chambers.

4. A device as claimed in claim 1, wherein a vent system is provided in said rotor.

5. A device as claimed in claim 4, wherein said vent system comprises an overflow chamber, an overflow channel communicating between said overflow chamber and at least one of said processing chambers, and a vent channel communicating between said overflow chamber and the atmosphere.

6. A device as claimed in claim 1, wherein said rotating means comprises a variable speed motor.

7. A device as claimed in claim 1, wherein said receiving means comprises a disk, said disk being removably mountable on said rotor and comprising a plurality of radial bores for removably receiving said radially disposed capillaries and holding said capillaries in register with said processing chambers.

8. A method for automated processing and separation of an unmeasured sample of whole blood into multiple aliquots of plasma, comprising the steps of:
   (a) providing a rotor having a central axis, a sample chamber, a plurality of removable capillary tubes, and means for receiving a plurality of capillaries disposed radially around said central axis, with said capillaries each having a radially outwardly oriented end and a radially inwardly oriented end, said rotor defining a plurality of processing chambers disposed around the circumference of said rotor so as to register with the outward ends of capillaries received in said receiving means, and a plurality of transfer channels each communicating between said sample chamber and one of said processing chambers;
   (b) introducing a sample of whole blood into said sample chamber;
   (c) rotating said rotor at a speed sufficient to distribute the blood radially outward from the sample chamber through the transfer channels into the processing chambers, and therein to centrifugally separate the blood into a plasma component and a solid cellular component;
   (d) reducing the rotation speed of said rotor to allow the plasma component to backfill into the capillaries;
   whereby the capillaries are filled with aliquots of plasma which may be used for further analyses.

9. A method as claimed in claim 8, wherein said rotor has a diameter from about 1 to 15 inches and is rotated at a speed of about 2400 to 3500 revolutions per minute for about 3 to 7 minutes so as to centrifugally separate the sample of whole blood into a solid component and a plasma component.

10. A method as claimed in claim 9, wherein said rotor has a diameter of about 3 inches and is rotated at a speed of about 3000 revolutions per minute for about 5 minutes so as to centrifugally separate the sample of whole blood into a solid component and a plasma component.

11. A method as claimed in claim 8, wherein said rotor further defines a circumferential distribution channel disposed around the circumference of said rotor and communicating between said transfer channels and said processing chambers.

12. A method as claimed in claim 8, wherein said rotor further defines a plurality of downwardly outwardly slanting cell chambers, each of said cell chambers communicating with one of said processing chambers.

13. A method as claimed in claim 8, wherein said rotor further comprises a vent system.

14. A method as claimed in claim 13, wherein said vent system comprises an overflow chamber, an overflow channel communicating between said overflow chamber and at least one of said processing chambers, and a vent channel communicating between said overflow chamber and the atmosphere.

15. A method as claimed in claim 8, wherein said receiving means comprises a disk, said disk being removably mountable within said rotor and comprising means for removably receiving said radially disposed capillaries and holding said capillaries in register with said processing chambers.

* * * * *